United States Patent [19]

Birk

[11] Patent Number: 5,962,414
[45] Date of Patent: Oct. 5, 1999

[54] MODIFIED BOWMAN-BIRK INHIBITOR

[76] Inventor: Yehudith Birk, 57 Hanasi Harishon Street, Rehovot, Israel

[21] Appl. No.: 08/979,552

[22] Filed: Nov. 26, 1997

[51] Int. Cl.$^6$ .............................. A61K 38/00; C07K 1/00
[52] U.S. Cl. ................................ 514/12; 514/2; 530/324; 530/345; 530/402; 530/406
[58] Field of Search .......................... 514/2, 12; 530/345, 530/324, 402, 406

[56] References Cited

U.S. PATENT DOCUMENTS 5,616,492    4/1997    Kennedy et al. ...................... 435/341

OTHER PUBLICATIONS

Seidl et al., Biochim. Biophys. Acta, 251(1), "Identification of the Trypsin–Reactive Site of the Bowman–Birk Soybean Inhibitor", pp. 83–93, in Chem. Abstr., 76:43286, 1971.

Madar, Z., Br. J. Nutr., 42(1), "Kinetics of Native and Modified Bowman–Birk Soybean Trypsin Inhibitor on Growth and Enzymes Activities of the Chick Pancreas", pp. 121–126, in Chem. Abstr. 92:1386, 1979.

Smirnoff et al., Int. J. Pept. Protein Res., 26(3), "Preparation of Photoreactive Derivatives of Trypsin–Chymotrypsin Inhibitors from Soybeans and Chick Peas by Selective Modification of Lysine Residues", pp. 274–278, in Chem. Abstr. 103:209708, 1985.

Birk et al., Adv. Exp. Med. Biol., 199(Nutr. Toxicol. Signif. Enzyme Inhib. Foods), "Photoreactive, Active Derivatives of Trypsin and Chymotrypsin Inhibitors from Soybeans and Chickpeas", pp. 469–481, in Chem. Abstr., 107:35681, 1986.

Ohba et al., Biosci., Biotechnol., Biochem., 62(6), "Cytotoxicity Induced by Erythrina Variegata Serine Proteinase Inhibitors in Tumor Hematopoietic Stem Cell Lines", pp. 1166–1170, inChem. Abstr. 129:197697, Jun. 1998.

Kay, UCLA–12–1167, "Structure–Function Relationships of Proteinase from Soybean (Bowman–Birk) and Lima Bean: Modification by N–Acetylimidazole", in Chem. Abstr. 92:2267, 1978.

Kay, E., J. Biol. Chem., 254(16), "Structure–Function Relationships of Proteinase Inhibitors from Soybean (Bowman–birk) and Lima Bean. Modification by N–Acetylimidazole", pp. 7648–7650, Aug. 1979.

Sarma et al., Indian J. Biochem. Biophys., 28(5–6), "Nature of the Tryptic/Chymotryptic Inhibitor from Horsegram (Dolichos Biflorus)", pp. 418–424, in Chem. Abstr. 116:79139, 1991.

Ekrami et al., FEBS Letters, 371(3), "Water–Soluble Fatty Acid Derivatives as Acylating Agents for Reversible Lipidization of Polypeptides", pp. 283–286, Sep. 1995.

Kay, E., J. Biol. Chem., 254(16), "Lima Bean Proteinase Inhibitor. Origins of Circular Dichroism Bands and Modification by Br2–and (CNS)2–", pp. 7643–7647, Jun. 1976.

*Primary Examiner*—Jon P. Weber
*Attorney, Agent, or Firm*—Bacon & Thomas

[57] ABSTRACT

Composition and method for suppression and inhibition of carcinogenesis comprising a modified Bowman-Birk inhibitor (BBI) comprising an active chymotrypsin inhibitory site, and a deactivated trypsin inhibitory site. The modified Bowman-Birk Inhibitor has been prepared by specifically acetylating a lysine residue with acetic anhydride.

9 Claims, No Drawings

MODIFIED BOWMAN-BIRK INHIBITOR

FIELD OF THE INVENTION

This invention relates to a modified Bowman-Birk Inhibitor (BBI), its preparation and its use as a food additive and pharmaceutical agent.

BACKGROUND OF THE INVENTION

The Bowman-Birk proteolytic enzyme inhibitor (BBI) is a designation of a family of stable low molecular weight trypsin and chymotrypsin enzyme inhibitors found in soybeans and various other seeds, mainly leguminous seeds, and vegetable materials. The Bowman-Birk enzyme inhibitor was first noted by Bowman (Proc. Soc. Exptl. Med. 1946, 63, 574) and subsequently purified and characterized by Birk, Y. (Biochim. Biophys. Acta 1961, 54, 378–381) and Birk. Y. et al, (1968) Biochemical Preparations Vol.12, 25–29 (W.E.M. Lands, Ed.) John Wiley & Sons Inc., later to be known and referred to as the Bowman-Birk Inhibitor (BBI), (hereinafter designated "BBI"). The BBI was reviewed by Kobayashi et al., J. Biochem. 1982, 91, 1511; by Birk, Int. J. Peptide Protein Res. 1985, 25, 113; and by Birk, pp. 257 in Hydrolytic Enzymes, Neuberger and Brocklehurst (Eds.), Elsevier Science Publications B.V., Amsterdam, 1987. The BBI is a protein characterized by its low molecular weight of ~8000 (in non-associated monomers), high concentration (~20%) of cystine, high solubility, resistance to heat denaturation and having the capacity to inhibit trypsin and chymotrypsin at independent inhibitory sites.

It is known that both crude and purified BBI prevent, or reduce various types of induced malignant transformation of cells in culture and experimental animals. There are also known various methods of obtaining crude and purified BBI products. A review of the relevant literature is provided by Kennedy et al. in U.S. Pat. No. 5,338,547, which is hereby incorporated in its entirety.

In view of the possibility that a BBI product may provide a potential remedy for prevention and amelioration of carcinogenesis, attempts have been made to prepare pure and sundry BBI preparations as potential therapeutic medicaments for diverse cancer conditions by various methods (U.S. Pat. No. 5,217,717 and U.S. Pat. No. 5,338,547). Preparing pure BBI, however, involves costly techniques.

It is now generally accepted that the responsibility for the suppression or inhibition of carcinogenesis, or the malignant transformation of cells from normal cells to cancer cells by BBI is due mainly to the chymotrypsin inhibitory site of the BBI molecule and not to the trypsin inhibitory site, (Yavelow et al., Proc. Natl. Acad. Sci. USA 1985, 82, 5395; Kennedy, Carcinogenesis 1985, 6, 1441; and Kennedy, pp. 9 in Protease Inhibitors as Cancer Chemopreventive Agents, Troll and Kennedy [Eds.], Plenum Press, New York, 1993).

The above mentioned U.S. Pat. No. 5,338,547, discloses a method for suppressing and inhibiting carcinogenesis with highly active BBI concentrate products wherein the level of biological activity is measured by chymotrypsin inhibitor content. These BBI concentrate products are made from acidic soybean solubles obtained from defatted soybean flour or flakes which were extracted with aqueous acid at pH 4 to 5, and from which the insolubles were removed by centrifugation. The soybean solubles were subjected to ultrafiltration to produce a crude BBI concentrate, which was diluted and spray dried to produce the final dried BBI concentrate product. In a preferred process embodiment disclosed in this patent the crude BBI concentrate is treated with acetone to produce a BBI concentrate precipitate which is air dried, ground, reslurried with water, filtered and then lyophilized or spray dried to produce the final BBI concentrate product. This product is stated to be an improved inhibitor of carcinogenesis. Kennedy et al. also mention that the BBI concentrate product can be further purified, by a method described by Odani et al. (J. Biochem. 1973, 74, 857), which method involves fragmenting the BBI product into two separated fragments, one fragment having the trypsin inhibitory site and the other fragment having the chymotrypsin inhibitory site. The inhibiting activity of the fraction having the chymotrypsin inhibitory site was, however, severely impaired.

It is known that ingesting products having a trypsin inhibitory effect such as the Kunitz Inhibitor and the BBI can have considerable deleterious consequences. These products can cause enlargement of the pancreas and increase of pancreatic proteolytic activity. On the other hand, the chymotrypsin inhibitory site on the BBI molecule does not cause pancreatic hypertrophy and has no significant effect on the amount of pancreatic proteinases (Pfeifer et al., J. Mol. Cell. Cardiol. 1981, 12, 37). This was demonstrated by Madar et al., Comp. Biochem. Physiol. 1974 48B, 251, by blocking the trypsin inhibitory site and comparing the blocked product with an unblocked product for pancreatic hypertrophy. Various blocking methods were used by Madar et al. Among these were the maleylation and succinylation of the BBI with maleic and succinic anhydride respectively.

SUMMARY OF THE INVENTION

It is an object of the present invention to provide a modified BBI composition for the suppression and inhibition of carcinogenesis.

Another object of the invention is to provide a simple and low cost method for the manufacture of a modified BBI composition from a wide range of raw materials.

A further object of this invention is to provide a simple and novel method, for modifying BBI to eliminate or significantly reduce therefrom the deleterious trypsin inhibitory effect.

DETAILED DESCRIPTION OF THE INVENTION

In accordance with the present invention there is provided a modified Bowman-Birk inhibitor (BBI) for suppression and inhibition of carcinogenesis characterized in that the BBI has an active chymotrypsin inhibitory site, and a deactivated trypsin inhibitory site.

The modified BBI according to the present invention is prepared by selectively deactivating the trypsin inhibitory site while leaving the chymotrypsin inhibitory site intact.

A preferred method of selectively deactivating the trypsin inhibitory site is by acylation. Acylation of BBI selectively blocks the trypsin inhibitory site without affecting the chymotrypsin inhibitory site. Acylation can be accomplished by the methods of Butler et al, Biochem. J. 112, 679–699 and Madar et al, Comp. Biochem. Physiol., 1974, vol. 48B, pp. 251–256.

Any known agent for acylating amino groups can be used in the present invention. Thus inorganic and organic acylation agents can be used, however, organic agents are preferred. Among the organic acylation agents, carboxylic acid anhydrides are preferred. These include monocarboxylic or polycarboxylic acid anhydrides. Representative monocarboxylic anhydrides are those derived from acetic acid, propionic acid, butyric acid, valeric acid, benzoic acid and the higher carboxylic acids such as the fatty acids. Among the polycarboxylic acid anhydrides are maleic anhydride, succinnic anhydride, phthalic anhydride, to mention a few. The choice of acylating agent will depend on the degree of completion of reaction, simplicity of method, cost and acceptability of acylated BBI compound for therapeutic use. For practical purposes acetic anhydride is the preferred acylating agent.

The BBI raw material for modification in accordance with this invention can be derived from a wide range of leguminous seeds and vegetable materials such as soybeans, chickpeas, limabeans, et cetera, and derived products of the same, that contain BBI. Typical raw materials can be soya flours or flakes, chickpea flour, limabean flour, soy whey made from industrial soy protein concentrate and isolate production and from traditional soy protein processes effluents. In a preferred embodiment of this invention defatted or low fat raw material is to be used.

The starting raw material containing BBI should be brought into an aqueous solution. If the raw material is a virtually dry material, such as defatted soya flour, it should preferably be milled first, then dispersed in water to provide a solution of the solubles fraction containing the BBI. The aqueous solution is then centrifuged or filtered to obtain a clear solution of the solubles fraction containing the BBI. This solution is passed through an affinity chromatography column that binds the BBI molecules to the column, the non-BBI components of the solution are washed out of the column. The bound BBI that remains on the column is then eluted from the column by acidic wash. A highly purified BBI containing solution is obtained. This purified BBI solution is then acylated, such as by acetylation, maleylation or succinylation, with acetylation being the more preferred method. The acylation takes place only at the trypsin inhibitory site of the BBI, masking and deactivating it, while leaving the chymotrypsin inhibitory activity site unreacted. The resultant BBI is thus free of deleterious trypsin inhibitory activity. The wet modified BBI is now dried, preferably by spray drying or freeze drying to attain a dry and practically pure modified BBI. Such modified BBI is effective as a remedy for prevention and amelioration of carcinogenesis without the trysin related side effects.

The invention will be illustrated by the following non-limiting examples.

EXAMPLE 1

Modified BBI from soybeans having chymotrypsin inhibitory activity, free of trypsin inhibitory activity was prepared from defatted soybean flour by the following processing steps: Soybean flour was extracted by water at 1:10, w/v ratio with stirring at room temperature for 2 hours. The mixture was centrifuged to obtain a crude BBI containing soluble supernatant fraction. This supernatant fraction was bound on an agarose-α chymotrypsin affinity column and purified BBI was eluted under acidic conditions. The trypsin inhibitory site of the BBI was masked and deactivated by acylation with acetic anhydride as follows. The neutralized solution of the purified BBI (0.1%) was reacted with aqueous acetic anhydride (2:100, v/v) for 30 min at 0° C. and filtered on a G-10 Sephadex column. The resulting filtrate was a "Modified BBI" having chymotrypsin inhibitory activity free of trypsin inhibitory activity. This modified BBI was dried by lypholyzation, to give dried modified BBI.

EXAMPLE 2

Modified BBI from chick peas having chymotrypsin inhibitory activity free of trypsin inhibitory activity was prepared from pulverized chickpea flour by the following processing steps: Pulverized chickpea flour was extracted with water at 1:10, w/v ratio by stirring at room temperature for 2 hours. The mixture was centrifuged to give a supernatant fraction containing a soluble crude product of the BBI family having trypsin and chymotrypsin inhibitor sites. This fraction was passed over either an agarose-α chymotrypsin affinity or an agarose trypsin column and the purified BBI was eluted from the column under acidic conditions. Masking and deactivating the trypsin inhibitory site on the purified BBI was accomplished by acylation via acetic anhydride as follows: A neutralized solution of the purified BBI (0.1%) was reacted with acetic anhydride (2:100, v/v) for 30 min at 0° C. The reaction product was filtered on a G-10 Sephadex column and dried by lypholyzation, to obtain modified BBI having active chymotrypsin inhibitory sites free of trypsin inhibitory activity.

EXAMPLE 3

A semi-purified modified BBI from soybeans having chymotrypsin inhibitory activity but no trypsin inhibitory activity was prepared from defatted soybean flour by the following processing steps: Soybean flour was extracted with water at 1:10, w/v ratio by stirring at room temperature for 2 hours. The mixture was centrifuged to give a supernatant fraction containing soluble crude BBI product. This soluble supernatant fraction was then heated at 100° C. for 30 minutes to inactivate the Kunitz trypsin inhibitor. The extract was then recentrifuged and the clear solution reacted with acetic anhydride (2:100, v/v) for 30 minutes at 0° C. The product was then separated from the reagent by filtration on a G-10 Sephadex column yielding a solution of semi-purified modified BBI having a chymotrypsin inhibitory activity free of trypsin inhibitory activity. This semi-pure modified BBI was dried by lypholyzation, to obtain dried semi-purified modified BBI.

Verification of the efficacy of the modified BBI of Examples 1–3 is achieved by the following methods:

In-Vitro

The C3H10T1/2 cell transformation assay is used as described by Yavelow, et al, 1985, PNA s82, 5395–5399.

In-Vivo

The modified BBI is orally administered to carcinogenesis induced hamsters as described by Kennedy, AR, in U.S. Pat. No. 5,338,547, Example B.

It should be understood from the above description and examples that there are many variations and modes to provide for a modified BBI, without departing from the spirit of the invention, on condition that the fundamental principles of the preparation of a novel modified BBI as a potential remedy for prevention and amelioration of carcinogenesis, as set forth above is followed.

I claim:

1. A composition for suppression and inhibition of carcinogenesis comprising a modified Bowman-Birk inhibitor (BBI) comprising an active chymotrypsin inhibitory site, and a deactivated acetylated trypsin inhibitory site which has been acetylated by acetic anhydride.

2. A dietetic supplement to inhibit carcinogenesis in animals susceptible to cancer comprising:
    a modified Bowman-Birk inhibitor (BBI) composition comprising an active chymotrypsin inhibitory site and a deactivated trypsin inhibitory site according to claim 1 formulated in a suitable dietary composition.

3. A food article comprising a modified Bowman-Birk inhibitor (BBI) composition comprising an active chymotrypsin inhibitory site and a deactivated trypsin inhibitory site according to claim 1.

4. A method for preparing a modified Bowman-Birk inhibitor (BBI) composition, comprising:
    acetylating a BBI containing solution containing chymotrypsin and trypsin inhibitory sites with acetic anhydride to selectively acetylate and deactivate the trypsin inhibitory site only, and recovering the modified BBI product.

5. A method as in claim 4, wherein the BBI containing solution is a purified BBI containing solution.

6. A method as in claim 5, wherein the BBI containing solution is purified by binding it on an affinity chromatography column, washing out the non-BBI components from the column and subsequently eluting the purified BBI inhibitor from the column.

7. A method as in claim 4, wherein the Bowman-Birk inhibitor (BBI) solution is derived from a vegetable material containing proteinase inhibitors of the BBI family.

8. A method as in claim 7, wherein the vegetable material is selected from soybeans, chickpeas, limabeans, defatted soybean flours, soybean whey, effluents generated from soy milk, tofu, soy isolates and soy concentrate processing.

9. A method for inhibiting carcinogenesis in an animal which is susceptible to cancer comprising:
    administering to said animal an effective amount of a modified Bowman-Birk inhibitor (BBI) composition comprising an active chymotrypsin inhibitory site and a deactivated acetylated trypsin inhibitory site which has been acetylated by acetic anhydride.

* * * * *